United States Patent [19]

Scott

[11] Patent Number: 4,871,916

[45] Date of Patent: Oct. 3, 1989

[54] SENSING OF METHANE

[75] Inventor: John C. Scott, Merewether, Australia

[73] Assignee: The Broken Hill Proprietary Company Limited, Victoria, Australia

[21] Appl. No.: 191,241

[22] Filed: May 6, 1988

[30] Foreign Application Priority Data

May 8, 1987 [AU] Australia ............................ PI1808/87

[51] Int. Cl.⁴ ................................................ G01J 1/00
[52] U.S. Cl. ................................................ 250/338.5
[58] Field of Search ....................................... 250/338.5

[56] References Cited

U.S. PATENT DOCUMENTS

| 3,998,557 | 12/1976 | Javan | 250/338.5 |
| 4,450,356 | 5/1984 | Murray et al. | 250/338.5 |
| 4,489,239 | 12/1984 | Grant et al. | 250/338.5 |
| 4,520,265 | 5/1985 | Griggs et al. | 250/338.5 |
| 4,555,627 | 11/1985 | McRae, Jr. | 250/338.5 |

Primary Examiner—Janice A. Howell
Assistant Examiner—T. Nguyen
Attorney, Agent, or Firm—Armstrong, Nikaido, Marmelstein, Kubovcik & Murray

[57] ABSTRACT

A spectroscopic method of sensing the presence of methane in an atmosphere includes directing through the atmosphere light emitted by a neodymium laser at a wavelength having a fluorescence linewidth which embraces at least one significant absorption line of the $v_2+2v_2$ band of methane.

8 Claims, 3 Drawing Sheets

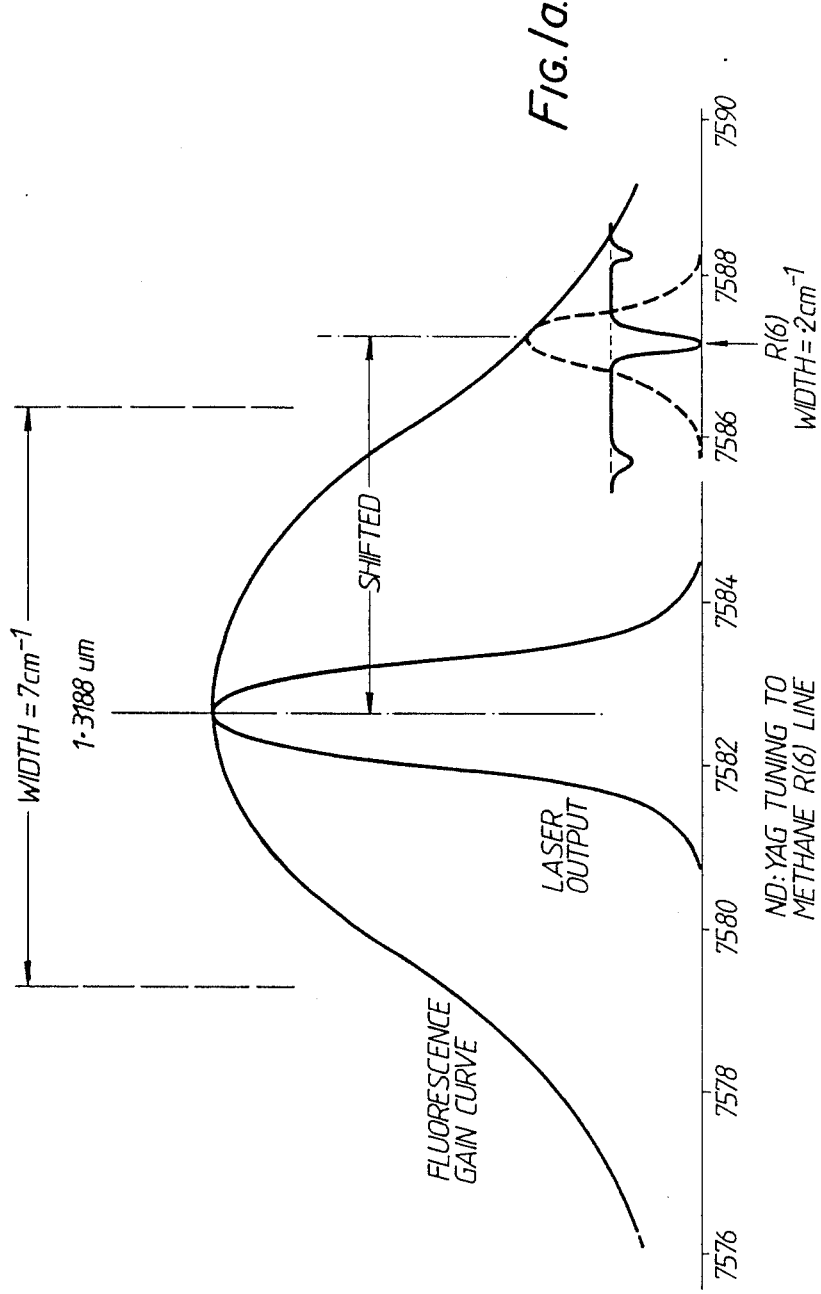

SENSING OF METHANE

BACKGROUND OF THE INVENTION

1. Field of the Invention

This invention relates to the sensing of methane in an atmosphere and has particular, though not of course exclusive, application to the remote sensing of methane at a facility such as a port or mine. The object of such sensing is to become aware when the amount of methane present is approaching an explosive or otherwise dangerous level.

2. Description of the Related Art

It is known to employ spectroscopic techniques to sense the presence of methane in an atmosphere. Past proposals have included the use of a He:nE laser to detect the strong 3.39 $\mu$m absorption line (U.S. Pat. No. 3,998,557), an Er: YAG laser tuned at 1.645 $\mu$m (Watkins et al, Rev. Sci Instrum (1981) 52(111), 1682), and an InGaAsP semiconductor laser to detect the $v_2+2v_3$ absorption band around 1.33 $\mu$m. (Chan et al, Applied Optics, (1983) 22(23), 3802). None of these proposals has proven entirely satisfactory for wide commercial application. The strong absorption lines of methane, e.g. the 3.39 $\mu$m line, have not been suitable for remote sensing over considerable distances such as at a port facility or open cut mine as the absorption by nearer methane masks the position at a greater distance. The various lasers suggested suffer from one or more of several disadvantages including inadequate power, high cost and insufficient ruggedness.

SUMMARY OF THE INVENTION

It is therefore an object of the invention to achieve an improved combination of laser emission band and methane absorption band which is better capable of practical application in a commercial methane sensing arrangement. The inventors have realized that the objective can be achieved by the combination of a specially tuned neodymium laser and the largely overlooked $v_2+2v_3$ methane absorption band, previously only suggested with an InGaAsP semiconductor laser.

BRIEF DESCRIPTION OF THE DRAWINGS

FIG. 1a is a wavenumber diagram for a Nd:YAG laser, also showing the R(6) absorption line of methane;

DESCRIPTION OF THE PREFERRED EMBODIMENTS

The invention accordingly provides a spectroscopic method of sensing the presence of methane in an atmosphere, comprising directing through the atmosphere light emitted by a neodymium laser at a wavelength having a fluorescence linewidth which embraces at least one significant absorption line of the $v_2+2v_3$ band of methane, and monitoring said light after traversal of the atmosphere to detect said absorption line(s).

The $v_2+2v_3$ band of methane is an overtone combination band in the near infrared region around 1.33 $\mu$m, arising from the fundamental molecular vibration $v_2=1533.3$ cm$^{-1}$ and $v_3=3018.9$ cm$^{-1}$.

The distance traversed by the light in the atmosphere of interest is at least 15 m, most preferably in the range up to 200 m.

The invention further provides apparatus, for example lidar apparatus, for spectroscopically sensing the presence of methane in an atmosphere, comprising a neodymium laser tuned to emit at a wavelength having a fluorescence linewidth which embraces at least one significant absorption line of the $v_2+2v_3$ band of methane, detection means to receive and monitor light to detect said absorption line(s) in the received light, and means to direct light emitted by the laser through the atmosphere to the detection means.

The laser may be a neodymium in yttrium aluminium garnet (Nd:YAG) laser, which is a well known rugged commercial laser, modified to emit at 1.318 $\mu$m (7581 cm$^{-1}$), which emission line arises from the transition $R_2 \rightarrow X_1$, has a lasing linewidth of the order of 1 cm$^{-1}$ and a fluorescence linewidth of about 7 cm$^{-1}$, adequate to embrace the R(6) absorption line of the $v_2+2v_3$ band at 7585.80 wavenumber.

Figure 1B:
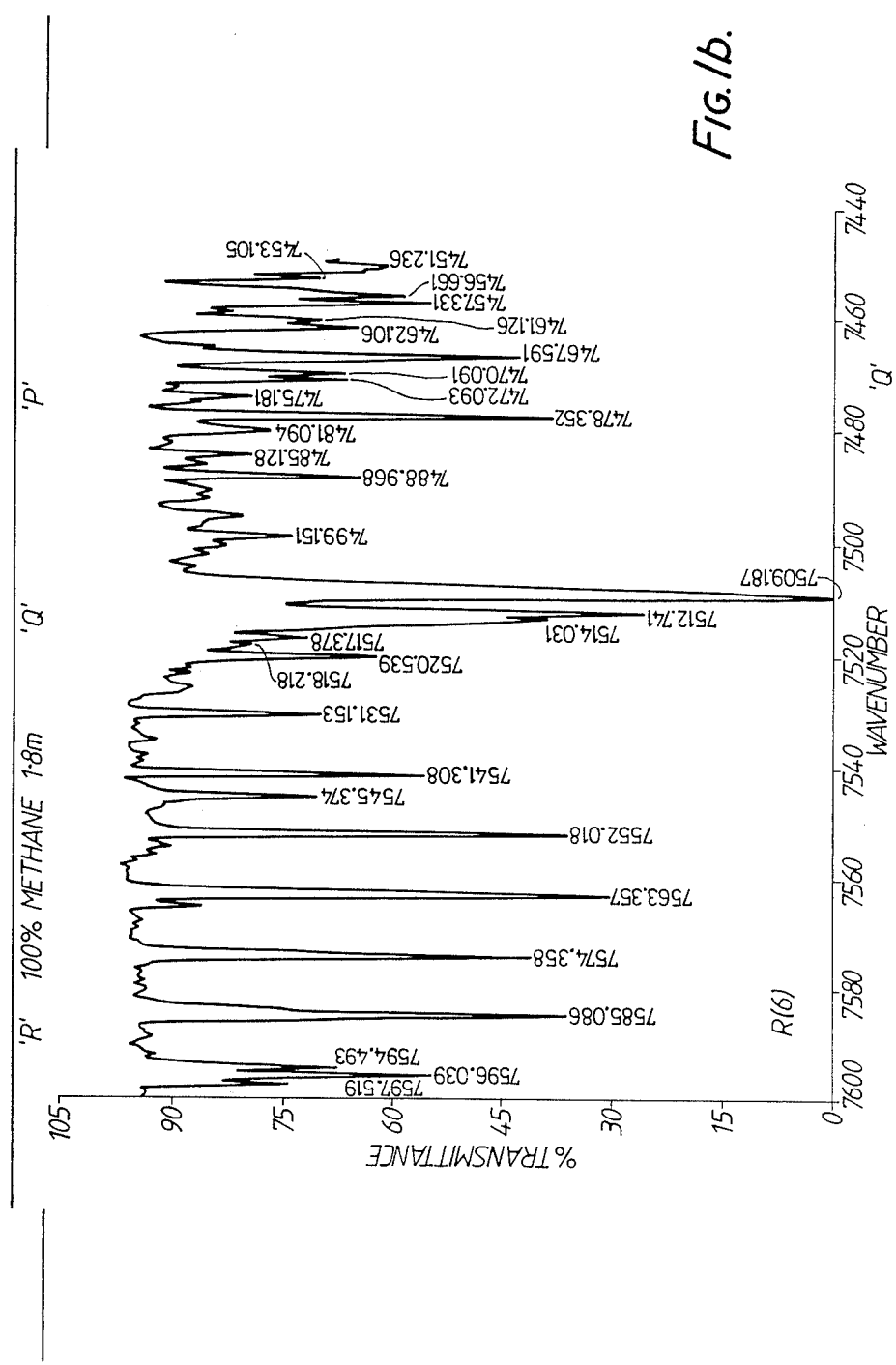
FIG. 1b is a detail of the R, Q, P branches of the $v_2+2v_3$ absorption band of methane.

FIG. 1 depicts this spectroscopic coincidence. FIG. 1a shows the locations of the 1.318 $\mu$m emission line and the R(6) absorption line on a wavenumber diagram, while FIG. 1b details the R, Q and P branches of the $v_2+2v_3$ methane absorption band.

Alternatively, the laser may be a neodymium in glass (Nd:GLASS) laser modified to emit in the region of 1.333 $\mu$m, which emission line has a lasing line width of several cm$^{-1}$ and a fluorescence linewidth of some 200 cm$^{-1}$. This line can be accurately tuned to embrace the Q branch of the $v_2+2v_3$ band, including the absorption line at 7509.9 wavenumber.

Modification or tuning of these lasers, which usually emit at 1.064 $\mu$m, can be achieved by tuning elements such as etelons and/or diffraction gratings, for example an intra cavity air spaced etelon, under computer control via a stepper motor. Laser wavelength may be monitored using a small low-resolution spectrometer (to confirm operation at the desired wavelength) and a photoacoustic cell containing methane.

The neodymium:YAG laser is a well proven rugged laser of high power output. The R(6) line and Q branch peak line of the $v_2+2v_3$ methane absorption band, and other lines in the band of similar peak amplitude, are found to have amplitudes which are in an ideal compromise range: sufficiently high to permit reliable and accurate line detection at reasonable cost, especially with a neodymium laser as emission source, but sufficiently low to allow the method to be applied to range resolved remote sensing over substantial distances, e.g. up to 200 meters, or even of a kilometre or several kilometers, such as is required at facilities like ports, mines and gas storage sites. The Q branch is considered to be especially attractive and the Nd:GLASS laser required to monitor this line can be readily derived from a commercial Nd:YAG laser by substituting the yttrum aluminium garnet (YAG) host material with a suitably selected glass.

Figure 2:
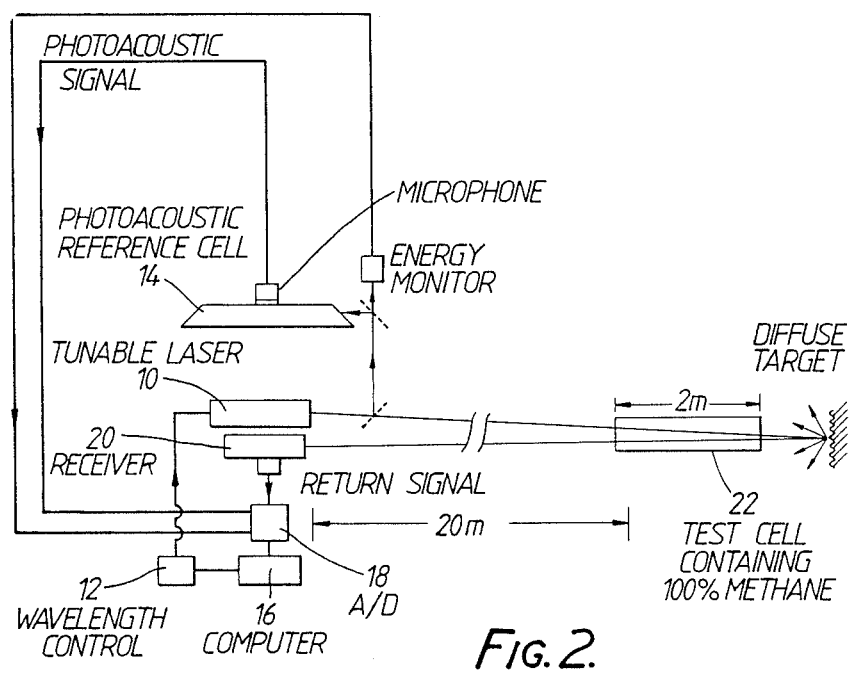
FIG. 2 is a diagram depicting an exemplary remote sensing spectrometer arrangement.
Figure 3:
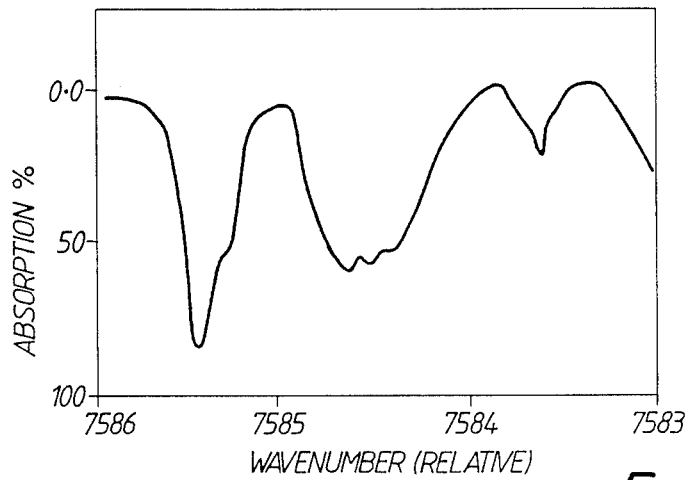
FIG. 3 is a computer-smoothed plot of absorption against wavenumber for the device shown in FIG. 2.

FIG. 2 is a diagram depicting an exemplary remote sensing spectrometer arrangement along the lines already described. The spectrometer includes a Nd:YAG laser 10, an etelon wavelength tuner 12, a photoacoustic reference cell 14, and a controlling computer device 16 with an analog/digital interface 18 to cell 14 and a receiver detector 20. FIG. 3 is a computer-smoothed plot of absorption against wavenumber for the spectrometer of FIG. 2, employing a 100% methane test cell 22, 2.0 m long×300 mm diameter, disposed 20 meters from the laser and 5 meters in front of a diffuse target 24. Approximately 90% absorption was obtained at the largest methane peak, corresponding to an absorption coefficient of $0.01\% cm^{-1}$.

It will be understood that, in accordance with known spectroscopic techniques, the concentration of methane in the atmosphere can be determined from the detected absortion signal and the known strength of the line.

Several conventional lidar (i.e. laser radar) configurations can be used to implement the spectroscopic coincidence of the invention to form a range resolved methane remote sensing instrument. By tuning the radiation on and off absorption a conventional differential absorption lidar will produce range resolved concentrations of methane in the atmosphere using aerosol scattering. The general principles of such a lidar configuration are disclosed, e.g., in Force et al, Applied Optics 24(17) at 2837 in connection with remote sensing of atmospheric ammonia with a $CO_2$ differential absorption lidar system. A second and uncommon technique involves so called wedge absorption where the spectral width of the laser output is arranged to be greater than the methane line width. This together with the spiky nature of the laser output means that for each laser pulse several hundred spectroscopic measurements are made, producing a wedge. The wedge absorption technique is described, e.g., in Watkins et al, supra, in connection with remote sensing of methane with an Er:YAG laser.

Typically, in a practical installation, the apparatus is configured or programmed to generate an alarm or control signal when the methane concentration in the atmosphere under surveillance exceeds a specific threshold. This threshold concentration is usually selected as indicative that the methane is approaching an explosive or otherwise hazardous or unacceptable level in the atmosphere.

The location of a methane concentration above threshold may be determined by time of flight measurement techniques using suitably modulated or pulsed light transmissions.

I claim:

1. A spectroscopic method of sensing the presence of methane in an atmosphere, comprising directing through the atmosphere light emitted by a neodymium laser at a wavelength having a fluorescence linewidth which embraces at least one significant absorption line of the $v_2+2v_3$ band of methane, and monitoring said light after traversal of the atmosphere to detect said absorption line(s) for. the presence of methane in the atmosphere traversed by the emitted light.

2. A spectroscopic method according to claim 1 wherein the neodymium laser utilised is a Nd:YAG laser modified to emit at 1.318 μm which emission arises from a transition $R_2 \rightarrow X_1$.

3. A spectroscopic method according to claim 1 wherein the neodymium laser utilised is a Nd:GLASS laser modified to emit at 1.333 μm.

4. A spectroscopic method according to claim 1 wherein the distance traversed by said light in said atmosphere is at least 15 meters.

5. A spectroscopic method according to claim 1, wherein the distance traversed by said light in said atmosphere is up to 200 meters.

6. Apparatus for spectroscopically sensing the presence of methane in an atmosphere, comprising a neodymium laser tuned to emit at a wavelength having a fluorescence linewidth which embraces at least one significant absorption line of the $v_2+2v_3$ band of methane, detection means to receive and monitor light to detect said absorption line(s) in the received light, and means to direct light emitted by the laser through the atmosphere to the detection means.

7. Apparatus according to claim 6 wherein said neodymium laser is a Nd:YA laser modified to emit at 1.318 μm, which emission arises from a transition $R_2 \rightarrow X_1$.

8. Apparatus according to claim 6 wherein said neodymium laser is a Nd:GLASS laser modified to emit at 1.333 μm.

* * * * *